United States Patent [19]

Holtkamp, Sr.

[11] Patent Number: Plant 7,102

[45] Date of Patent: Jan. 9, 1990

[54] AFRICAN VIOLET PLANT NAMED LITTLE TOURMALINE

[76] Inventor: Reinhold Holtkamp, Sr., Werther Strasse 112, D4294 Isselburg, Fed. Rep. of Germany

[21] Appl. No.: 310,376

[22] Filed: Feb. 15, 1989

[51] Int. Cl.[4] ..... A01H 5/00
[52] U.S. Cl. ..... Plt./69
[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Little Tourmaline characterized by its miniature growth habit; semi-double, dark pink flowers with elongated petals; strong stems which curve toward the center to form a compact bouquet above the leaves; profuse and continuous flowering; bright green, heart- to spear-shaped leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha,* and hereinafter referred to by the cultivar name Little Tourmaline.

The new cultivar was referred to during the breeding and selection process by the designation K 1/65 and is a product of a planned breeding program. The new cultivar was originated from a cross made by me in the controlled breeding program in Haffen, Federal Republic of Germany. The female, or seed parent was a cultivar designated 4 Mini. The male, or pollen parent was a cultivar designated 43.

Little Tourmaline was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Little Tourmaline has not been observed under all possible environmental conditions. The phenotype may vary significantly with variations in environment such as temperature, light intensity and day length. The following observations, measurements and values describe the new cultivar as grown in a 4 cm pot in Haffen, West Germany and Nashville, Tenn. under greenhouse conditions which closely approximate those generally used in commercial practice.

The following traits have been repeatedly observed and are determined to be basic characteristics of Little Tourmaline, which in combination distinguish this african violet as a new distinct cultivar:

(1) Little Tourmaline will not grow taller than 8 cm.

(2) Semi-double dark pink flowers with elongated petals.

(3) Strong wirelike and upright flower stems curving toward the center.

(4) First flash of flowers form a tight bouquet above the leaves.

(5) Profuse flowering; under good growing conditions continuous flowering.

(6) Each plant carries 10–12 and more upright flower stems each of which carries 4–5 and more flowers.

(7) Long lasting, non-dropping flowers.

(8) Plant saleable 10 to 11 weeks after planting of unrooted shoot.

(9) Seed capsules push slightly through.

(10) Bright green, hairy leaves.

(11) Heart- to spear-shaped leaves are 2.0 to 2.8 cm in size.

(12) After maturity the flowers dry off, and remain on the peduncle.

The new cultivar is most similar to Little Kuzite, also a miniature cultivar of applicant and disclosed in a pending application. Similarities are the leaf and flower color. However, Little Tourmaline has semi-double blooms with elongated petals, whereas Little Kunzite has single, violet-shaped flowers with an intensive pink touch in the center.

The accompanying color photographic drawing shows a typical specimen plant of the new cultivar grown in a 4 cm pot. The plant is pictured next to a pencil, highlighting the miniature size and growth habit of Little Tourmaline. The colors appearing in the photograph are as true as possible with color illustrations of this type.

In the following description, color references are made to The Royal Horticultural Society Colour Chart (RHS), except where general colors of ordinary significance are referred to. Color values were taken under natural sunlight conditions at approximately 1 p.m. in Nashville, Tenn.

Botanical classification: *Saintpaulia ionantha,* Ramat., c.v. Little Tourmaline.

Parentage:

*Male parent.*—43.

*Female parent.*—4 Mini.

Propagation: The new cultivar holds its distinguishing characteristics through successive propagations by leaf cuttings.

Plant: From 7 cm to 8 cm tall when grown in pots, and approximately 8–11 cm in diameter when fully grown.

*Leaves.*—General form: Heart-to spear-shaped. Diameter: 20–24 mm wide and 25–28 mm long. Texture: Leatherlike. Aspect: Shiny, hairy. Veins: Upperside: visible; underside; well pronounced, light green, shiny. Color (upperside: Between Yellow-Green Group 146 A and 147 A.

Color (underside): Greyed-Green Group 193 A with occasional touches of Greyed-Purple Group 187 A. Very young leaves are Greyed-Purple 187 A. Petiole: Strong, green with reddish brown touch, hairy.

*Flowers.*—Buds: Size: 3–4 mm just before opening. Shape: Bell-shaped. Color: Purplish green. Sepals: Five (5). Color: Brownish green. Calyx: Shape: Funnel-shaped. Aspect: Spear-shaped, hairy. Peduncle: Character: Strong upright, hairy. Color: Reddish brown. Individual flowers: Size: 25–28 mm. Shape: Semi-double, violet-shaped (having up to 15 petals). Color (upperside): Purple Group 78 A. Under cooler temperatures and more intensive lighting, the pink tends to intensify. Color (underside): Purple Group 78 B to C. Borne: Each flower stem carries 4–5 and more flowers on strong, upright peduncle that are free standing above the leaves, thereby forming a compact bouquet. Flowering habit: Flowers 10–11 weeks after planting an unrooted plantlet.

Reproductive organs.—Stamens: Two (2). Anthers: 2 composed of 4 anther cells, seed capsule pushes slightly through. Filaments: Yellowish green, 2–3 mm long. Styles: 5–6 mm long, purplish pink, base of ovary light green and hairy.

*Roots.*—Normally developed, white when young, turning slightly brownish when older.

Disease resistance: Good.

General observations: Little Tourmaline is a super miniature violet, which does not grown taller than 8 cm. The semi-double flowers have up to 15 elongated petals and are dark pink. The flowers are long-lasting and non-dropping. Under good growing conditions Little Tourmaline will bloom continuously. A nice bouquet of flowers free standing above the bright green, heart- to spear-shaped leaves develops approximately 10–11 weeks after planting an unrooted plantlet. Each of the 10–12 and more strong flower stems carries 4–5 and more flowers.

I claim:

1. A new and distinct cultivar of African violet named Little Tourmaline, as described and illustrated, and particularly characterized by its miniature growth habit; semi-double, dark pink flowers with elongated petals; strong stems which curve toward the center to form a compact bouquet above the leaves; profuse and continuous flowering; bright green, heart-to spear-shaped leaves; flowering 10–11 weeks after planting of unrooted shoot, and by its long lasting and non-dropping flowers.

* * * * *

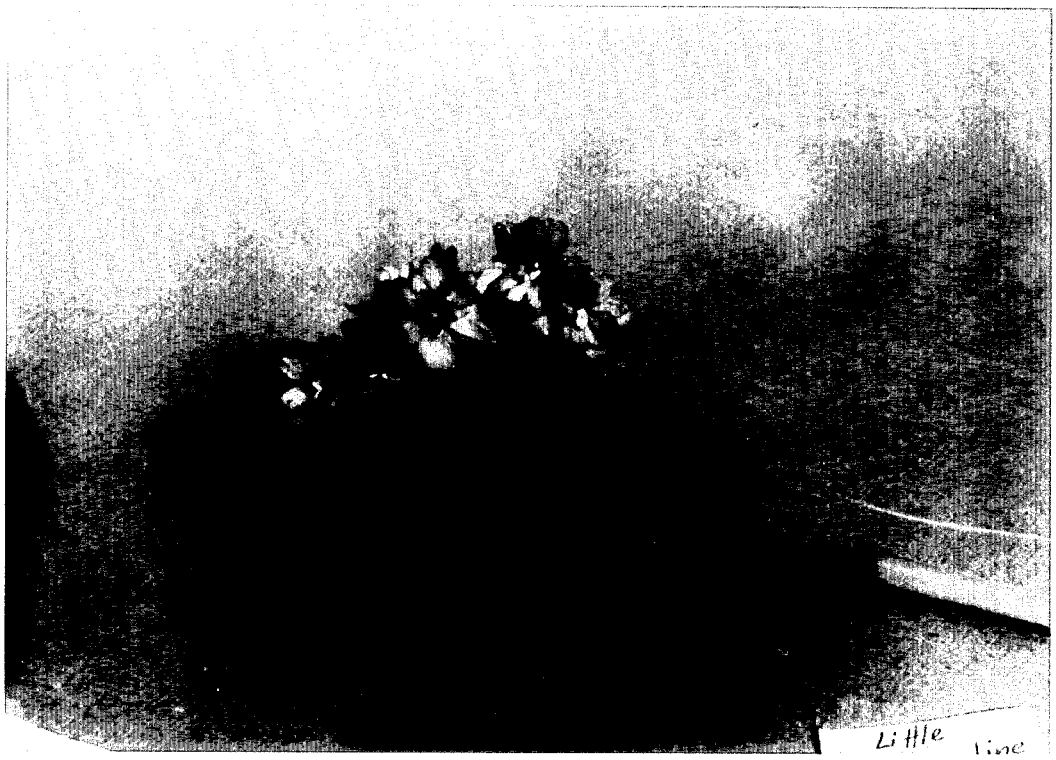
Little